United States Patent [19]

Wong et al.

[11] Patent Number: 6,114,588

[45] Date of Patent: Sep. 5, 2000

[54] HYDROFORMYLATION OF ALPHA-ALCOHOL-DIOLEFINS TO DIALCOHOLS

[75] Inventors: Pui-Kwan Wong, Houston; Andrew Allison Moxey, Richardson, both of Tex.

[73] Assignee: Shell Oil Company, Houston, Tex.

[21] Appl. No.: 09/096,075

[22] Filed: Jun. 11, 1998

Related U.S. Application Data

[60] Provisional application No. 60/049,287, Jun. 11, 1997.

[51] Int. Cl.[7] .................................................. C07C 45/00
[52] U.S. Cl. ......................... 568/451; 568/454; 568/462; 568/458; 568/494
[58] Field of Search .................................... 568/454, 451, 568/494, 458, 462

[56] References Cited

U.S. PATENT DOCUMENTS

| | | | |
|---|---|---|---|
| 2,327,066 | 8/1943 | Roelen et al. | 260/598 |
| 3,239,569 | 3/1966 | Slaugh et al. | 260/632 |
| 3,351,666 | 11/1967 | Mertzweiller | 260/604 |
| 4,248,802 | 2/1981 | Kuntz | 568/454 |
| 4,539,306 | 9/1985 | Chang | 502/154 |

FOREIGN PATENT DOCUMENTS

2243639  9/1990  Japan .

*Primary Examiner*—James O. Wilson
*Attorney, Agent, or Firm*—Del S. Christensen

[57] ABSTRACT

A method to produce dialcohols is provided, the method comprising the steps of:

providing a feed stream comprising an alpha-alcohol-diolefin;

reacting the feed stream with hydrogen and carbon monoxide in the presence of a catalyst system comprising a cobalt phosphine ligand complex under conditions effective to hydroformylate at least a portion of the diolefin in the feed stream; and recovering the dialcohol from the reacted feed stream. This method is a one-step process to hydroformylate alpha-alcohol-diolefins such as 2,7-octadien-1-ol to produce a significant yield of dialcohols such as 1,9-nonanediol.

18 Claims, No Drawings

HYDROFORMYLATION OF ALPHA-ALCOHOL-DIOLEFINS TO DIALCOHOLS

RELATED APPLICATIONS

This application is a continuation of provisional application Ser. No. 60/049,287 filed on Jun. 11, 1997.

FIELD OF THE INVENTION

The invention relates to a method to produce dialcohols from diolefins having terminal alcohol groups.

BACKGROUND OF THE INVENTION

Hydroformylation reactions, commercially known as the oxo process, were discovered by O. Roelin in Germany and patented in 1943 (U.S. Pat. No. 2,327,066). The oxo process utilizes a cobalt catalyst, HCo (CO)$_4$, in the presence of syn gas having a 1:1 hydrogen to carbon monoxide ratio at a pressure of about 200 atmospheres, and at a temperature between about 120° C. and 140° C.

This hydroformylation results in the addition of hydrogen and carbon monoxide to the olefin to form an aldehyde. The aldehyde may then be reduced to form an alcohol.

Diolefins may be converted to dialcohols by this method. The dialcohols can be useful, for example, as monomers for condensation polymerization with diesters to form polyesters.

An improvement to the oxo process has been disclosed in U.S. Pat. No. 3,239,569. This improvement involved modification of the oxo catalyst with a phosphine ligand to form a cobalt complex. This improvement results in a significant yield of alcohol products directly from the hydroformylation without the need for a separate reduction step.

The oxo process has also been improved with respect to selectivity to straight chained alcohol or aldehyde products as suggested in U.S. Pat. No. 4,539,306. Patent '306 suggests that linear aldehydes or alcohols from olefins may be preferentially produced using a mixed transition metal hydroformylation catalyst wherein the catalyst comprises a mixture of transition metal compounds wherein the first component is an anionic transition metal catalyst having a charge of at least −2. The formula of the anionic compound is generally defined as $M^{+n}[H_yA_xL_z]^{-n}$ wherein A represents Fe, Ru, Os, W, Cr, Co, Rh, Ir, or Mo, M is a cationic species, n is an integer greater than or equal to 2, x is an integer greater than or equal to 1, y is an integer greater than or equal to 0 and z is an integer generally corresponding to the number of available coordination bonding sites of A. The component L is a Group VIII compound, preferably a halide or carbonyl of the Group VIII compound.

The mixed transition metal hydroformylation catalyst of U.S. Pat. No. 4,539,306 is not suggested to be selective to alcohols over aldehydes, but alcohols are preferentially produced by increasing the reaction temperature or the residence time. Increasing the residence time and/or the temperature is an unacceptable method to increase selectivity to linear alcohols because increasing side reactions compete with reduction of aldehydes to alcohols and limit the ultimate yield of linear alcohols.

1,9-Nonanediol can be produced by a method suggested in Japanese patent publication No. 2-243639 by hydroformylation of 2,7-octadien-1-ol using a rhodium catalyst system, and subsequent hydrogenation of the hydroformylation product. Considerably operating and capital costs are incurred by the additional hydrogenation step of the process of this patent publication.

Therefore there remains a need for a process to produce dialohols from starting materials such as alpha-alcohol-diolefins such as 2,7-octadien-1-ol wherein a increased residence time or temperature is not needed and wherein a one-step process can be utilized, and it is an object of the present invention to provide such a process.

SUMMARY OF THE INVENTION

This and other objects are achieved by a process to produce dialcohols such as 1,9-nonanediol from alpha-alcohol-diolefins such as 2,7-octadien-1-ol, the process comprising the steps of:

providing a feed stream comprising an alpha-alcohol-diolefin;

reacting the feed stream with hydrogen and carbon monoxide in the presence of a catalyst system comprising a cobalt phosphine ligand complex under conditions effective to hydroformylate at least a portion of the diolefins in the feed stream; and recovering dialcohols from the reacted feed stream.

This method provides a significant yield of dialcohols and accomplishes this with a single step process, i.e., no separate hydrogenation step is required to convert aldehyde intermediate products to alcohols.

The phosphine is preferably a trialkyl phosphine, and the alkyl groups of the trialkylphosphine are preferably alkyls containing greater than six and more preferably six to twelve carbon atoms each.

The preferred alpha-alcohol-diolefin is 2,7-octadien-1-ol, which is readily prepared by the dimerization of butadiene and is readily hydroformylated to 1,9-nonanediol by the present invention.

1,9-nonanediol is useful, among other things, as a monomer for condensation polymerization with diesters to form polyesters.

DESCRIPTION OF A PREFERRED EMBODIMENT

The feed stream that is preferably hydroformylated by the present invention is a product of dimerized butadienes.

Dimerizing 1,3-butadiene in the presence of water results in 2,7-octadien-1-ol, which is commercially available.

Catalyst complexes suitable for practice of the present invention are known and commercially available from many sources. The phosphines ligands may include alkyl groups that are the same, or are different, and that vary in length. Preferably, the alkyls have at least six carbon atoms, and more preferably between six and twelve carbon atoms. Trialkylphosphines with relatively small alkyl groups are more reactive, and must be handled with greater care in order to not lose some of the ligand by degradation or reaction with oxygen. Ligands with at least six carbon atoms are therefore preferred because of their improved stability.

The phosphine may be primary, secondary or tertiary, which is preferred. Suitable phosphines include those of the general formula:

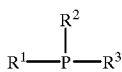

in which $R^1$, $R^2$ and $R^3$ each independently represent an optionally substituted alkyl group, an optionally substituted cycloalkyl group or an optionally substituted aryl group or $R^2$ and $R^3$ together represent an optionally substituted alkylene or phosphacycloalkylene group. Preferably, a suitable alkyl group has up to 20 carbon atoms, a suitable cycloalkyl group up to 5 to 7 carbon atoms in the ring and a suitable aryl group up to 18 carbon atoms in the ring and may optionally be a hetroaryl ring. A suitable aryl group may be, for example, an anthryl, naphthyl or a phenyl group, which is preferred. Phosphines of the general formula I in which $R^1$ and $R^2$ each represent an optionally substituted phenyl group are a preferred group of phosphines. Within this group, those phosphines in which $R^3$ also represents an optionally substituted phenyl group are particularly preferred. Very good results have been obtained with triphenylphosphine.

An optionally substituted alkylene group formed by $R^2$ and $R^3$ suitably has in the range of from 4 to 9 and particularly from 6 to 8 carbon atoms, and such a group may form a monocyclic or a bicyclic ring containing the phosphorous atom. An example of such a compound is

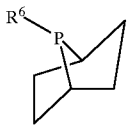

in which $R^6$ is a $C_6$ to $C_{20}$ hydrocarbyl group.

Another preferred group of organic phosphines are those of the general formula I in which $R^3$ represents a chain of carbon atoms ending with the group —$PR^4R^5$, in which $R^4$ represents an optionally substituted phenyl group and $R^5$ an optionally substituted alkyl, optionally substituted cycloalkyl or optionally substituted phenyl group. Within this group, $R^1$ and $R^2$ preferably represent an optionally substituted phenyl group. Preferred compounds are 1,5-di(diphenylphosphino)pentane and 1,6-di(diphenylphosphino) hexane. Preferably, $R^4$ and $R^5$ are equal to $R^1$ and $R^2$, respectively. The chain of carbon atoms suitably comprises 2 to 6 carbon atoms and preferably comprises 2 to 6 methylene groups.

An aryl group present in the organic phosphine of the catalytic system may carry an electron-donating substituent, such as an alkyl group, a p-alkoxy group (para with respect to the carbon-phosphorous bond) and a dialkylamino group. The alkyl groups and p-alkoxy groups preferably have no more than 5 carbon atoms; examples of such groups are methyl, ethyl, propyl, isopropyl, butyl, sec-butyl and tert-butyl groups. An example of a suitable phosphine is tri(p-methoxyphenyl)phosphine.

The phosphines used in the process according to the invention may carry electron-withdrawing substituents on any aryl group. Examples of electron-withdrawing substituents are halogen atoms and m-alkoxy and halomethyl groups, "halo" referring to iodo, bromo, chloro and fluoro; the halomethyl groups include mono-, di- and trihalomethyl groups. An example of a suitable phosphine is tri(p-chlorophenyl)phosphine.

Other examples of suitable phosphines are phenyldiethylphosphine, ethyldiphenylphosphine, phenyldipropylphosphine, propyldiphenylphosphine, tri-o-tolylphosphine, phenyl-di-butylphosphine, diphenylmethylphosphine, tricyclohexylphosphine, tri-n-butylphosphine and tri-n-octylphosphine. Further examples of suitable phosphines are 1,2-di(diphenylphosphino) ethane, 1,2-di(diphenylphosphino)ethene, 1,2-di(diphenylphosphino)ethylene, 1,2-di(diphenylphosphino)-benzene,1,2-diphenylphosphinotetrafluoro-1,2-cyclobutene, 1,2-diphenylphosphino-hexafluoro-1,2-cyclopentene, 1,2-diphenylphosphino-octafluoro-1,2-cyclohexene, 1,4-diphenyl-1,4-diphosphacyclohexane, bis(o-diphenylphosphinophenyl)phenylphosphine and tris(o-diphenylphosphinophenyl)phosphine.

Mixtures of two or more organic phosphines may be used.

Catalyst complexes useful in practice of the present invention may be prepared by methods disclosed in, for example, U.S. Pat. No. 3,239,569, the disclosure of which is incorporated herein by reference. These complexes have the general formula of:

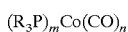

where: R is a hydrocarbonyl group (the same or different groups); and m and n are integers, each having a value of at least one and whose sum is four.

The hydrocarbonyl groups of the phosphine are preferably alkyls containing greater than six and more preferably six to twelve carbon atoms each. The alkyl groups may be the same or different groups, and two or more may be connected, forming a cyclic alkly group.

The suitable catalyst complexes may comprise two or more of the $(R_3P)_mCo(CO)_n$ groups. For example, the complex between cobalt, carbon monoxide, and the trialkyl phosphine may be monomeric in structure or may be composed of several monomeric units, such as a dimer of this compound.

A suitable catalyst complex may be prepared by, for example, combining an organic or inorganic salt of cobalt with the desired phosphorus-containing ligand. Suitable cobalt salts include, for example, cobalt carboxylates, such as acetates, octanoates, as well as cobalt salts of mineral acids such as chlorides, sulfates, or sulfonates. The valence state of the cobalt may then be reduced and the cobalt-containing complex formed by heating a solution of the components in the presence of hydrogen and carbon monoxide. The organic or inorganic salt of cobalt and the phosphorus-containing ligand could optionally be combined in the presence of the feed stream containing the dienol, and the catalyst complex thereby formed as the hydroformylation is taking place.

The residence time required for the hydroformylation reaction of the present invention is generally between about 12 and about 48 hours, and is preferably between about 20 and about 24 hours. The hydroformylation is preferably carried out at a temperature between about 100° C. and about 200° C., and more preferably between about 150° C. and about 170° C. The hyroformylation is preferably carried out between about with a carbon monoxide partial pressure of between about 350 and about 550 psia, with a hydrogen to carbon monoxide molar ratio of between about 1:1 and about 2:1. The amount of cobalt utilized in the catalyst complex is preferably sufficient to result in the cobalt to ligand ratio of between about 1:1 and about 1:3. These variable are, of course, interdependent, and many different combinations can be found to be acceptable by routine experimentation. The chosen conditions are preferably such that at least about 50 percent of the diolefins of the feed stream are hydroformylated to dialcohols.

The hydroformylation of the present invention is preferably carried out in an organic solvent, and a preferred organic solvent is diglyme. The present invention, when carried out in a diglyme solvent has been found to result in greater conversion to diols when compared to other solvents, such as toluene/water, toluene, N,N-dimethylformamide (DMF), or decane. The weight percent of the diolefin in the solvent is preferably between about 20 and about 50 percent.

In general, higher temperatures reduce required residence time, increased the amounts of byproducts produced, and have been found to be detrimental to linearity of the products.

Dialcohol products of the present invention can be separated from the reaction mixture by, for example, distillation.

EXAMPLE 2,7 Octadiene-1-ol was hydroformylated using cobalt hydroformylation catalysts according to the following procedure. Dicobalt octacarbonyl (0.046 grams, or 0.267 mmol cobalt), tri-n-octylphosphine (0.0992 grams, or 0.267 mmol), 2,7-octadiene-1-ol (5.0 grams, or 39.7 mmol), and 15 ml of diglyme were charged to a 100 ml stainless steel Parr Reactor inside a drybox. The reactor was sealed and removed from the drybox. The mixture was heated to 150° C., pressurized to 1000 psi with 1:1 syn gas and stirred for 24 hours under these conditions. At the end of this period, the reactor was cooled, purged with nitrogen and the reaction mixture was analyzed by GC. Yield of difunctional hydroformylation products was 50.3% and yield of reduction products was 39.5%, based on moles of 2,7-octadiene-1-ol, and no measurable 2,7-octadiene-1-ol was observed in the product.

Reduction products included 1-octanol and octanal, and hydroformylation products included C9 diols, dialdehyde, and hydroxy-aldehydes, in relative amounts of about 70, 10 and 20, respectively, with greater than 90% linearity.

Comparative Examples—Other Metals

Different hydroformylation catalysts were tested, including (1) a platinum-based catalyst prepared by adding platinum acetylacetonate (0.12 grams, 0.308 mmole), 1,2-bis(9-phosphabicyclo[3.3.1]non-9-yl)ethane (0.115 grams, 0.369 mmole), mesitylenesulfonic acid (0.117 grams, 0.492 mmole), and 50 ml of diglyme; (2) a palladium-based catalyst prepared by mixing palladium acetate (0.113 grams, 0.5 mmole), 1,2-bis(9-phosphabicyclo[3.3.1]non-9-yl) ethane (0.214 grams, 0.7 mmole), sodium iodide (0.0374 grams, 0.25 mmole), trifluoromethanesulfonic acid (0.172 grams, 1.15 mmole), and 5 ml of deoxygenated sulfolane; and (3) a rhodium-based catalyst prepared by adding (1,5-cyclooctadiene)(2,4-pentanedionato)rhodium (0.031 grams, 0.01 mmole), triphenylphosphine (0.262 grams, 10 mmole), 2,7-octadiene-1-ol (12.0 grams, 100 mmole), and 40 ml of diglyme. Hydroformylation conditions for the platinum-based catalyst were 1000 psi with 2:1 ratio of hydrogen to carbon monoxide, at 115° C. for 24 hours. Hydroformylation conditions for the palladium-based catalyst were 1000 psi with 2:1 hydrogen to carbon monoxide ratio, at 105° C. for 24 hours. Hydroformylation conditions for the rhodium-based catalyst were 1000 psi with 1:1 hydrogen to carbon monoxide ratio, at 95° C. for 24 hours.

Products of hydroformylation with the palladium, rhodium, and platinum catalysts did not contain significant amounts of alcohols, but contained significant amounts of aldehydes. The products were then hydrogenated with a Calsicat nickel catalyst at 1000 psi hydrogen pressure, and 150° C. for about 16 hours. Even after hydrogenation, the products contained less than about of diols having nine carbon atoms.

Examples—Other Ligands 2,7-octadiene-1-ol was hydroformylated as in the example above with different ligands, and one comparative example was run with the original "Oxo" catalyst $(HCo(CO)_4)$ with no ligand. Ligands tested included tri-isobutylphosphine $(P(iPr)_3)$, tricyclohexylphosphine $(P(Cy)_3)$, 1,2-bis(dicyclohexylphosphino)ethane (1,2-bis[P(Cy)$_2$]C$_2$H$_4$), 1,2-bis(diphenylphosphino)ethane (1,2-bis[P(Ph)$_2$]C$_2$H$_4$), 1,2-bis(9-phospha-bicyclo[3.3.1]non-9-yl)ethane (BICYCLO-2), 1,3-bis(diphenylphosphino)proane (1,3-bis[P(Ph)$_2$]C$_3$H$_6$), 1,4-bis(diphenylphosphino)butane (1,4-bis[P(Ph)$_2$]C$_4$H$_8$), sodium diphenylphosphinobenzene sulfonate (Ph$_2$P(PhSO$_3$Na)), 2-diphenylphosphinopyridine (Ph$_2$PPyr), and triphenylphosphine (P(Ph)$_3$). Products, classified as hydroformylation products ("HF", including 1,9-nonanediol, 9-hydroxynonaldehyde, 1,9-nonanedialdehyde), reduction products ("RP", including 1-octanol and octane), and other ("OTH", mostly higher boiling condensation products) are listed below in the TABLE, along with the results from the example.

TABLE

| LIGAND | % HF | % RD | % OTH |
|---|---|---|---|
| $HCo(CO)_4$ | 17.2 | 69.6 | 13.2 |
| $P(iPr)_3$ | 31.8 | 61.3 | 6.9 |
| $P(Cy)_3$ | 26.3 | 65.3 | 8.6 |
| 1,2-bis[P(Ph)$_2$]C$_2$H$_4$ | 14.4 | 19.5 | 7.8 |
| BICYCLO-2 | 35.0 | 53.6 | 11.4 |
| 1,3-bis[P(Ph)$_2$]C$_3$H$_6$ | 36.5 | 54.1 | 9.4 |
| 1,4-bis[P(Ph)$_2$]C$_4$H$_8$ | 34.9 | 56.3 | 8.8 |
| Ph$_2$P(PhSO$_3$Na) | 35.2 | 53.8 | 11.0 |
| Ph$_2$PPyr | 40.8 | 49.2 | 10.0 |
| P(Ph)$_3$ | 37.7 | 46.9 | 15.4 |
| P(n-octyl)$_3$ | 50.3 | 39.5 | 10.2 |

From the TABLE, it can be seen that the hydroformylation products obtained using the cobalt phosphine ligand complex to catalyze the reaction generally contained considerably more hydroformylation products than products of the reaction using other catalyst systems.

We claim:

1. A method to produce a dialcohol, the method comprising the steps of:
    providing a feed stream comprising an alpha-alcohol-diolefin;
    reacting the feed stream with hydrogen and carbon monoxide in the presence of a catalyst system comprising a cobalt phosphine ligand complex under conditions effective to hydroformylate at least a portion of the alplha-alcohol-diolefin in the feed stream; and
    recovering dialcohols from the reacted feed stream.

2. The method of claim 1 wherein the phosphine ligand of the cobalt phosphine ligand complex is a trialkylphosphine ligand complex wherein each alkyl group contains at least six carbon atoms.

3. The method of claim 2 wherein the alkyl groups of the cobalt trialkylphosphine each contain between about six and about twelve carbon atoms.

4. The method of claim 1 wherein at least a portion of the diolefins in the feed stream is 2,7 octadiene-1-ol.

5. The method of claim 1 wherein the residence time for which the feed stream is reacted with hydrogen and carbon monoxide in the presence of the catalyst system comprising the cobalt phosphine ligand complex is between about 20 and about 24 hours.

6. The method of claim 1 wherein the temperature at which the feed stream is reacted with hydrogen and carbon monoxide in the presence of the catalyst system comprising the cobalt phosphine ligand complex is between about 150° C. and about 170° C.

7. The method of claim 1 wherein a reduction reaction step is not included in the method.

8. The method of claim 1 wherein the feed stream comprises between about 20 and about 80 percent by weight diglyme as a solvent.

9. The method of claim 8 wherein the molar ratio of phosphorous to cobalt in the catalyst complex is between about 1:1 and about 3:1.

10. The method of claim 1 wherein at least about 50% of the alpha-alcohol-diolefins are converted to dialcohols.

11. The method of claim 1 wherein the molar ratio of alpha-alcohol-diolefin to catalyst complex is between about 100:1 and about 500:1.

12. The method of claim 1 wherein the molar ratio of carbon monoxide to hydrogen is between about 1:2 and about 2:1.

13. The method of claim 4 wherein the residence time for which the feed stream is reacted with hydrogen and carbon monoxide in the presence of the catalyst system comprising the cobalt phosphine ligand complex is between about 10 and about 24 hours.

14. The method of claim 13 wherein the temperature at which the feed stream is reacted with hydrogen and carbon monoxide in the presence of the catalyst system comprising the cobalt phosphine ligand complex is between about 100° C. and about 200° C.

15. The method of claim 14 wherein a reduction reaction step is not included in the method.

16. The method of claim 15 wherein the feed stream comprises straight chained hydrocarbons having at least eight carbon atoms and at least two double bond between the carbon atoms.

17. The method of claim 16 wherein at least about 50% of the diolefins are converted to dialcohols having two more carbon atoms than the original diolefins.

18. The method of claim 17 wherein the molar ratio of diolefin to catalyst complex is between about 100:1 and about 500:1.

* * * * *